United States Patent [19]

Parker et al.

[11] 4,091,092

[45] May 23, 1978

[54] POLYMYXIN F AND PROCESS OF PRODUCING POLYMYXIN F

[75] Inventors: William L. Parker, Pennington; Edward Meyers, East Brunswick; Maxwell W. Nimeck, North Brunswick; William E. Brown, Princeton, all of N.J.

[73] Assignee: E. R. Squibb & Sons, Inc., Princeton, N.J.

[21] Appl. No.: 761,578

[22] Filed: Jan. 24, 1977

Related U.S. Application Data

[63] Continuation-in-part of Ser. No. 724,886, Sep. 20, 1976, abandoned.

[51] Int. Cl.$^2$ .............................................. A61K 35/00
[52] U.S. Cl. ...................................... 424/118; 195/96
[58] Field of Search .................. 195/96; 424/115, 118

[56] References Cited

PUBLICATIONS

Chemical Abstracts, vol. 81; 36490w; 1974.
Chemical Abstracts; vol. 81, 36491x; 1974.
Chemical Abstracts; vol. 81, 48534b; 1974.
Chemical Abstracts, vol. 83, 7138y; 1975.
Merck Index, 9th edition, pp. 984 and 985; 1976.

*Primary Examiner*—Alvin E. Tanenholtz
*Assistant Examiner*—Robert J. Warden
*Attorney, Agent, or Firm*—Lawrence S. Levinson; Merle J. Smith; Donald J. Barrack

[57] ABSTRACT

A mixture of antibiotic substances designated polymyxin F is obtained by the cultivation under controlled conditions of a strain of *Bacillus circulans*, and is active against gram-negative and gram-positive bacteria. This strain of *Bacillus circulans* has been deposited in the American Type Culture Collection as A.T.C.C. No. 31228.

2 Claims, 1 Drawing Figure

INFRARED SPECTRUM OF POLYMYXIN F HYDROCHLORIDE SALT IN POTASSIUM BROMIDE

POLYMYXIN F AND PROCESS OF PRODUCING POLYMYXIN F

This application is a continuation-in-part of U.S. patent application Ser. No. 724,886, filed Sept. 20, 1976 now abandoned.

SUMMARY OF THE INVENTION

A mixture of novel antibiotic substances of unknown chemical structure, designated polymyxin F, is obtained by cultivating a strain of the microorganism *Bacillus circulans* which has been deposited in the American Type Culture Collection as A.T.C.C. No. 31228. Polymyxin F is a mixture of three acyldecapeptides, said acyldecapeptides differing only in the acyl residue. The mixture of antibiotic substances is active against gram-negative and gram-positive bacteria.

DETAILED DESCRIPTION OF THE INVENTION

The Microorganism

Figure 1:
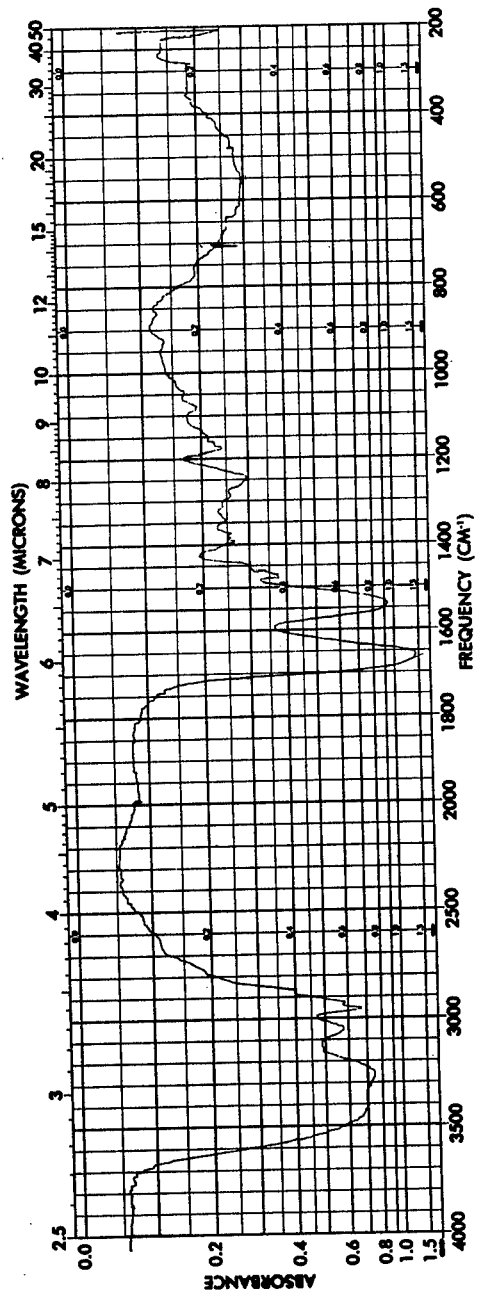
FIG. 1 shows the infrared spectrum of the hydrochloride salt of polymyxin F in potassium bromide.

The microorganism used for the production of polymyxin F is a strain of *Bacillus circulans* isolated from the soil. A subculture of the organism may be obtained from the permanent collection of the American Type Culture Collection, Rockville, Maryland. Its accession number in this repository is A.T.C.C. No. 31228.

The characteristics of *Bacillus circulans* A.T.C.C. No. 31228 are:

Microscopic: Spore forming bacillus that is gram variable to gram negative. Spores are central to subcentral. The sporangium is swollen. The vegetative rods are not in long chains and are motile. Rods are $0.5$–$0.7\mu \times 2.0$–$5.0\mu$ in size.

Macroscopic: In nutrient broth growth is faintly turbid and confined to the bottom of the tube. No pellicle is formed. No growth occurs above 50° C. On nutrient agar, after 3 days of incubation at 28° C, growth is thin and adherent to the agar. Occasionally rough and smooth variant colony types are seen within the same culture.

Physiological Characteristics: Catalase is produced. The Voges-Proskauer test for production of acetylmethylcarbinol is negative. The pH in Voges-Proskauer broth at 7 days is 4.5. Growth is positive on BBL anaerobic agar made without glucose or Eh indicator. Acid is formed from glucose, xylose, arabinose and mannitol, but no gas is produced up to 30 days. Crystalline dextrins are not produced. The test for production of dihydroxyacetone from glycerol is negative. Casein is not decomposed.

The above characteristics conform with those of *Bacillus circulans*, as cited in the monograph of the genus by Gordon, Haynes and Pang (1973), Agr. Handbook No. 427 "The Genus Bacillus", Agr. Res. Service, U.S.D.A.

Production of the Antibiotic

*Bacillus circulans* A.T.C.C. No. 31228 produces the antibiotic mixture polymyxin F which possesses activity against gram-negative and gram-positive bacteria. To form the antibiotic mixture polymyxin F according to the preferred method, *Bacillus circulans* A.T.C.C. No. 31228 is grown at, or near, room temperature (25° C) under submerged aerobic conditions in an aqueous nutrient medium containing an assimilable carbohydrate and nitrogen source. The fermentation is carried out until substantial antibiotic activity is imparted to the medium, usually about 60 to 120 hours, preferably about 90 hours.

After the fermentation is completed, the beer is acidified, preferably to about pH 2, with an acid such as concentrated hydrochloric acid. Filter aid is added to the acidified fermentation beer, and the whole suspension is filtered. The solids are liberally washed with water, and the washings are then pooled with the filtrate. The washed solids are discarded. The filtrate plus added washings are extracted with water-saturated n-butanol, the butanol extract is concentrated in vacuo at a temperature below 45° C to a small volume, and the concentrate is dissolved in a small volume of methanol. Polymyxin F is precipitated by the addition of acetone, and then washed with acetone and dried in vacuo. The precipitate is dissolved in water, absorbed on a weak acid ion-exchange resin, e.g., Amberlite IRC-50 resin ($Na^+$), at pH 6.0 to 7.5, and the antibiotic is eluted from the resin by suspending the resin in methanol-water (1:1) and adjusting the pH to about 1.0 with hydrochloric acid. Elution with methanol-water (1:1) adjusted to about pH 1.5 with concentrated hydrochloric acid is continued until all of the polymyxin F is removed from the resin. The combined eluate is concentrated in vacuo until the methanol is removed, the concentrate is adjusted to pH 10.5 with sodium hydroxide and polymyxin F is extracted into butanol. The butanol extract is washed with 1N hydrochloric acid and concentrated in vacuo. The residue is dissolved in methanol and polymyxin F is precipitated with ethyl acetate. The precipitate is washed with ethyl acetate and dried in vacuo, yielding partially purified polymyxin F. The partially purified antibiotic is dissolved in a mixture of water and methanol, absorbed on a column of carboxymethyl cellulose ($Na^+$), and eluted from the column with a sodium chloride gradient. Active fractions from the major antibiotic component are combined, acidified with 1N hydrochloric acid, and extracted with butanol. The butanol extract is concentrated in vacuo and polymyxin F hydrochloride is isolated by precipitation from methanol with ethyl acetate as described above.

Polymyxin F is a mixture of basic antibiotic substances that forms salts with various inorganic and organic acids. The hydrochloride, prepared by the above procedure, can be conveniently converted to any desired water-soluble salt using anion-exchange resins. Alternatively, the free base can be prepared by extracting a butanol solution of the hydrochloride with dilute aqueous sodium hydroxide and then removing the butanol in vacuo. Salts can be obtained from the residue by neutralization with the appropriate acid.

Acid hydrolysis of polymyxin F yields a mixture of 2,4-diaminobutyric acid (Dab), threonine (Thr), serine (Ser), isoleucine (Ile), leucine (Leu) and fatty acid in an approximate molar ratio of 5:1:1:1:2:1. The fatty acid is a mixture of 6-methyloctanoic acid, isooctanoic acid and octanoic acid. Polymyxin F is thus a mixture of three acyldecapeptides, the components of which differ in the acyl residue. The compositions and empirical formulae of these components are as follows:

| Polymyxin F$_1$ | Polymyxin F$_2$ | Polymyxin F$_3$ |
|---|---|---|
| Dab(5) | Dab(5) | Dab(5) |
| Thr(1) | Thr(1) | Thr(1) |
| Ser(1) | Ser(1) | Ser(1) |
| Ile(1) | Ile(1) | Ile(1) |
| Leu(2) | Leu(2) | Leu(2) |
| 6-Methyloctanoic acid(1) | Isooctanoic acid(1) | Octanoic acid(1) |
| $C_{54}H_{101}N_{15}O_{13}$ | $C_{53}H_{99}N_{15}O_{13}$ | $C_{53}H_{99}N_{15}O_{13}$ |

Polymyxin F$_1$ is the most abundant component and polymyxin F$_3$ the least abundant component. Each component has four primary amino groups (the γ-amino groups of four of the Dab residues) and no other ionic functionality. Polymyxin F forms acid salts having stoichiometry consistent with this chemical make-up.

the following example further illustrates the preparation of polymyxin F.

EXAMPLE 1

Yeast beef agar slants are seeded with *Bacillus circulans* A.T.C.C. No. 31228, incubated overnight at 30° C and used to inoculate 100 ml of an aqueous soybean meal medium contained in 500 ml Erlenmeyer flasks. The composition of the germination medium is:

| Medium | Grams |
|---|---|
| Glucose | 50.0 |
| Nutrisoy Flour | 15.0 |
| Soluble Starch | 15.0 |
| CaCO$_3$ | 10.0 |
| CoCl$_2$ . 6H$_2$O | 0.005 |
| Distilled water to | 1 liter |

The medium is sterilized for 30 minutes at 121° C and at 15 lbs steam pressure prior to use. The inoculated germination flasks are incubated at 25° C for 72 hours on a rotary shaker, operating at 280 r.p.m. with a 2-inch throw.

A 5% (v/v) transfer is made from the germination flasks to 10 liters of medium contained in a 14 liter glass vessel with the medium and operating conditions described below:

| | Medium | Grams |
|---|---|---|
| A. | Nutrisoy Flour | 150 |
| | Soluble Starch | 150 |
| | CaCO$_3$ | 100 |
| | CoCl$_2$ . 6H$_2$O | 0.05 |
| | Distilled water to | 9 liters |
| B. | Glucose, 50% in water | 1 liter |

The ingredients in A are sterilized separately from the glucose of B. Both are sterilized at 15 lbs. pressure at 121° C for 15 minutes prior to use. The inoculum, 500 ml, is added to 10 liters of medium and incubated 90 hours. During incubation, the broth is aerated at the rate of 1.4 volumes of air per volume of broth per minute and stirred at 750 rpm.

The fermentation broth (10 liters) is adjusted to pH 2.0 with concentrated hydrochloric acid (75 ml). The solids are separated by centrifugation at 9,000 rpm. and washed with two 1-liter portions of water. The washings are combined with the supernate to give 10 liters. The washed cake (750 g) is discarded.

The supernate (10 liters) is extracted three times with 3-liter portions of water-saturated n-butanol. The combined butanol extract (7 liters) is concentrated in vacuo, at a temprature less than 45° C., to a small volume (100 ml).

The butanol-extract concentrate from two 10-liter fermentations, obtained as described above, is diluted with methanol (300 ml) and added to 7.5 liters of acetone. The resulting precipitate is separated, washed with acetone, and dried in vacuo, giving 13.6 g of solid.

The acetone-insoluble powder, 13.6 g, is dissolved in 300 ml of water and stirred with 135 g of Amberlite IRC-50 ion-exchange resin (H+ form) for 12 hours, adding 5 N sodium hydroxide as necessary to maintain the pH between 6.0 and 7.5. The resin is separated, washed with methanol-water (1:1) and then stirred for 2 hr with 400 ml of methanol-water (1:1) maintaining the pH at 1.0 by the addition of concentrated hydrochloric acid. The slurry is then placed in a column and the resin eluted with methanol-water (1:1) adjusted to pH 1.5 with concentrated hydrochloric acid until the effluent from the column has negligible antibiotic activity. The combined eluate (ca. 600 ml) is concentrated in vacuo to remove the methanol, yielding an aqueous solution of polymyxin F.

An aqueous solution of polymyxin F is mixed with butanol and adjusted to pH 10.5 with 5N sodium hydroxide. The butanol phase is separated and washed twice with 0.01 N sodium hydroxide and then three times with 1N hydrochloric acid, back-extracting the acid washes with butanol. The combined butanol extract is concentrated in vacuo. The residue is dissolved in methanol and added to ethyl acetate. The resulting precipitate is washed with ethyl acetate and dried in vacuo giving 0.94 g of polymyxin F, which is dissolved in 35 ml of methanol-water, 5:2, and applied to a 2.5 × 50 cm column of Whatman CM52 carboxymethyl cellulose in the sodium form. The column is eluted at a rate of 3 ml/minute, first with 120 ml of water and then with a linear gradient prepared from 4 liters of 0.15N sodium chloride and 4 liters of 0.30N sodium chloride. Fractions are collected and assayed by paper-disc agar diffusion assay to locate the main antibiotic peak. The fractions comprising the main peak of activity are combined. The resulting solution is acidified with hydrochloric acid and washed with chloroform. The antibiotic is then extracted from the aqueous phase with butanol. The butanol is removed in vacuo and the residue converted to a powder, 0.44 g, by precipitation from methanol with ethyl acetate as described above.

Analysis: Calcd. for $C_{54}H_{101}N_{15}O_{13}$.4 HCl: C, 49.34; H, 8.05; N, 15.99; Cl, 10.79. Found: C, 49.68; H, 8.05; N, 16.13; Cl, 10.96.

The infrared spectrum of polymyxin F as the hydrochloride (1:4) in KBr is shown in FIG. 1.

The electrophoretic mobility of polymyxin F on paper, using a buffer consisting of 0.05M sodium formate in formic acid/t-butanol/water (1:2:7) is 0.84 relative to phloroglucinol as an electroosmotic indicator (mobility 0.0) and polymyxin B (mobility 1.00).

Paper-partition chromatography of polymyxin F on Whatman #1 paper, using the upper phase of butanol/acetic acid/water (4:1:5) gives an R$_f$ value of 0.72.

Polymyxin F is soluble in water and methanol and insoluble in acetone, ether, ethyl acetate, benzene and the like.

Hydrolysis of 0.09 mg of polymyxin F in 6N hydrochloric acid at 110° C for 16 hours yields a mixture containing 0.326 micromoles of 2,4-diaminobutyric acid, 0.066 micromoles of threonine, 0.063 micromoles of serine, 0.049 micromoles of isoleucine and 0.141 micromoles of leucine as shown by conventional Stein-Moore analysis. Gas chromatographic analysis also shows the presence, in descending quantity, of 6-methyloctanoic acid, isooctanoic acid and octanoic acid.

Specific rotations of polymyxin F hydrochloride (1:4) are as follows:

| λ | $[\alpha]^{22}$ | (c 0.5 in 0.5N HCl) |
|---|---|---|
| 589 nm | −43° | |
| 578 | −47° | |
| 546 | −54° | |
| 436 | −97° | |
| 365 | −160° | |

The melting point of polymyxin F hydrochloride (1:4), determined in an evacuated capillary, is 213° to 219° C.

The UV spectrum of polymyxin F hydrochloride (1:4) in water has no maximum at wavelengths greater than 200 nm; there is, however, end absorption with an $E_{1cm}^{1\%}$ at 220 nm of 47.

Biological Activity

Two-fold tube dilution assays with several microorganisms show the following results. The polymyxin F used in this study is the hydrochloride (1:4).

| Organism | MIC (μg/ml) |
|---|---|
| *Staphylococcus aureus* FDA 209P | 50 |
| *Streptococcus pyogenes* C 203 | 6.3 |
| *Escherichia coli* ATCC 10536 | 1.2 |
| *Escherichia coli* SC 8294* | 2.4 |
| *Pseudomonas aeruginosa* SC 8329* | 3.1 |

*Organisms from the Squibb Culture Collection

A comparison of the activities of polymyxins B and F show that polymyxin F has substantial activity against some organisms that are resistant to polymyxin B.

| Organism | MIC (μg/ml) | |
|---|---|---|
| | Polymyxin B | Polymyxin F |
| *Escherichia coli* SC8599* | 0.1 | 1.2 |
| *Escherichia coli* SC8600*[a] | >100 | 18.7 |
| *Escherichia coli* SC9251* | 0.06 | 0.4 |
| *Escherichia coli* SC9252*[b] | 18.7 | 9.4 |
| *Escherichia coli* SC9253*[b] | 50.0 | 12.5 |

*Organisms from the Squibb Culture Collection.
[a]Polymyxin-resistant variant of *E. coli* SC8599
[b]Polymyxin-resistant variants of *E. coli* SC9251

Testing with mice that had been infected intraperitoneally with *Escherichia coli* SC8294 suspended in 5% hog gastric mucin in an amount 500 times the $LD_{50}$ shows that 50% survive after subcutaneous injection of 4.2 mg/kg of polymyxin F hydrochloride (1:4) 1 hour post infection. None of the mice survive the infection when the antibiotic is not administered.

What is claimed is:

1. Polymyxin F, or an acid salt thereof, said polymyxin F being a mixture of three basic peptides comprising in an approximate molar ratio of 5:1:1:1:2:1 2,4-diaminobutyric acid, threonine, serine, isoleucine, leucine, and a mixture of the acyl residues of 6-methyloctanoic acid, isooctanoic acid and octanoic acid; polymyxin F hydrochloride (1:4) having the infrared spectrum in potassium bromide as shown in FIG. 1 and the following physical characteristics: approximate elemental analysis C, 49.68; H, 8.05; N, 16.13; Cl, 10.96; and melting point of about 213° C to 219° C, in vacuo.

2. A process for producing polymyxin F which comprises fermenting *Bacillus circulans* A.T.C.C. No. 31228 under submerged aerobic conditions in an aqueous nutrient medium comprising an assimilable carbon source and an assimilable nitrogen source.

* * * * *